United States Patent
Vinogradov et al.

(10) Patent No.: US 10,466,206 B2
(45) Date of Patent: Nov. 5, 2019

(54) NON DESTRUCTIVE MAGNETOSTRICTIVE TESTING WITH UNIDIRECTIONAL GUIDED WAVES GENERATED BY FERROMAGNETIC STRIP SENSOR

(71) Applicant: Southwest Research Institute, San Antonio, TX (US)

(72) Inventors: Sergey A. Vinogradov, San Antonio, TX (US); Glenn M. Light, San Antonio, TX (US); Charles E. Duffer, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 122 days.

(21) Appl. No.: 15/376,049

(22) Filed: Dec. 12, 2016

(65) Prior Publication Data
US 2018/0164256 A1 Jun. 14, 2018

(51) Int. Cl.
*G01N 29/24* (2006.01)
*G01N 29/04* (2006.01)
*G01D 5/14* (2006.01)

(52) U.S. Cl.
CPC .......... *G01N 29/2412* (2013.01); *G01D 5/14* (2013.01); *G01N 29/043* (2013.01); *G01N 2291/0425* (2013.01)

(58) Field of Classification Search
CPC ............. G01N 29/2412; G01N 29/043; G01N 29/265; G01N 29/04; G01N 29/28; G01N 29/041
See application file for complete search history.

(56) References Cited

U.S. PATENT DOCUMENTS

| | | | | |
|---|---|---|---|---|
| 4,021,728 A * | 5/1977 | Makino | ................ | B82Y 25/00 324/235 |
| 4,079,360 A * | 3/1978 | Ookubo | ................ | G01D 5/145 235/449 |
| 4,604,612 A * | 8/1986 | Watkins | ................ | B64D 15/20 340/582 |
| 5,017,907 A * | 5/1991 | Cordery | ................ | G01V 15/00 340/551 |
| 7,573,261 B1 * | 8/2009 | Vinogradov | ........... | G01N 27/82 324/240 |
| 8,079,266 B2 * | 12/2011 | Nichiforenco | ..... | G01N 27/9026 73/643 |
| 2004/0045373 A1 * | 3/2004 | Kwun | ..................... | G01L 3/102 73/862.331 |
| 2007/0090904 A1 * | 4/2007 | Kim | ........................ | B06B 1/08 335/205 |
| 2009/0174399 A1 * | 7/2009 | Vinogrador | ............ | G01N 27/82 324/238 |
| 2010/0052669 A1 * | 3/2010 | Kwun | .................. | G01N 29/043 324/240 |

(Continued)

*Primary Examiner* — Helen C Kwok
(74) *Attorney, Agent, or Firm* — Livingston Law Firm

(57) ABSTRACT

A ferromagnetic strip sensor for use in magnetostrictive testing of various structures. In its simplest form, the sensor has a ferromagnetic strip with an electrical coil winding. A permanent magnet is positioned atop the strip, aligned with but offset from, a center axis of the strip. The sensor is operable such that a time varying current in the coil results in a unidirectional guided wave. This guided wave travels within the structure, and is reflected from anomalies in the structure.

20 Claims, 9 Drawing Sheets

(56) References Cited

U.S. PATENT DOCUMENTS

| | | | | |
|---|---|---|---|---|
| 2010/0164486 A1* | 7/2010 | Giordano | ............... | D06F 37/302 |
| | | | | 324/207.25 |
| 2010/0259252 A1* | 10/2010 | Kim | ................. | B06B 1/085 |
| | | | | 324/240 |
| 2011/0169486 A1* | 7/2011 | Light | ................. | G01N 29/2412 |
| | | | | 324/240 |
| 2011/0221428 A1* | 9/2011 | Puchot | ................. | G01N 29/041 |
| | | | | 324/240 |
| 2013/0036822 A1* | 2/2013 | Daikoku | ............ | G01N 29/2412 |
| | | | | 73/632 |
| 2014/0312888 A1* | 10/2014 | Vinogradov | ....... | G01N 29/2412 |
| | | | | 324/240 |
| 2017/0023531 A1* | 1/2017 | Vinogradov | ....... | G01N 29/2412 |
| 2017/0155204 A1* | 6/2017 | Guo | ................. | H01R 13/04 |

* cited by examiner

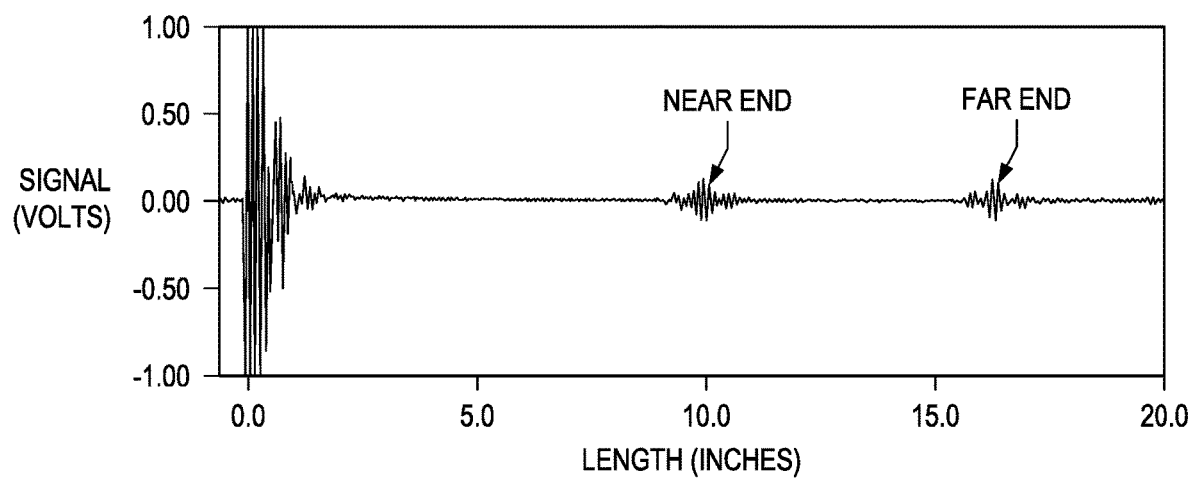
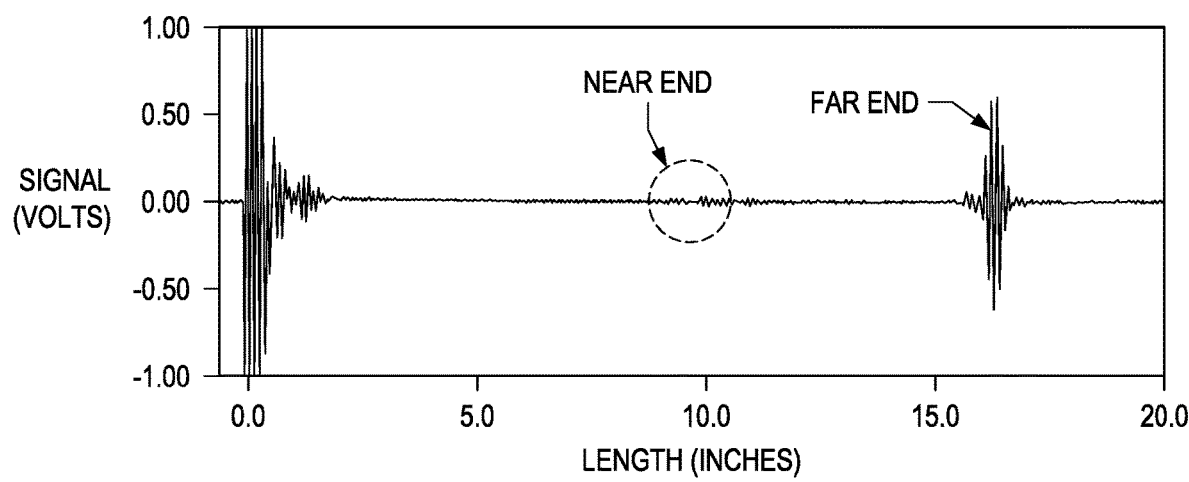
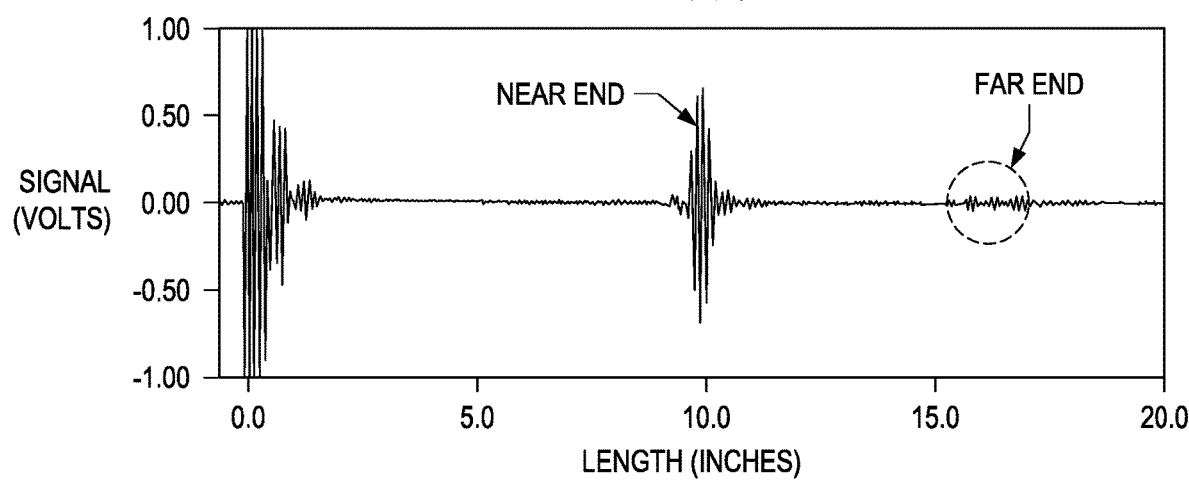

NON DESTRUCTIVE MAGNETOSTRICTIVE TESTING WITH UNIDIRECTIONAL GUIDED WAVES GENERATED BY FERROMAGNETIC STRIP SENSOR

TECHNICAL FIELD OF THE INVENTION

This invention relates to nondestructive testing using guided waves and magnetostrictive sensor technology, and more particularly, to generating unidirectional guided waves with a ferromagnetic strip sensor.

BACKGROUND OF THE INVENTION

Magnetostriction is a property of ferromagnetic materials that causes them to change shape when subjected to a magnetic field. Magnetostrictive materials can convert magnetic energy into kinetic energy, or the reverse, and are used to build various actuators and sensors.

For active magnetostrictive testing, elastic waves are launched and reflected echoes of the waves from defects such as corrosion or cracks are detected. Various magnetostrictive actuators have been designed to generate guided waves for testing various types of structures. The guided waves may be longitudinal, torsional, or shear, and the type of wave may depend on whether the structures are rods and cables, pipes, or plates.

Because many systems use the same device for actuating the guided waves as for receiving the reflected waves, magnetostrictive actuator/sensors are often referred to as simply "sensors". Combined actuator/sensor devices are also often sometimes referred to as "probes".

Ferromagnetic coupling of a magnetostrictive sensor to the material being tested is an important operative feature of magnetostrictive test systems. Some sensors may make use of magnetostrictive properties of the material being tested, and do not require a magnetostrictive coupling interface.

However, many sensors are made more effective, or are adapted for testing non-ferromagnetic metals, by mechanical coupling of a ferromagnetic material to the material being tested at areas where the sensors are to be placed. This may be achieved, for example, by coating the surface of the material to be tested with a coat of ferromagnetic material or by bonding a ferromagnetic medium to the surface of the material. Some sensors incorporate a ferromagnetic material into the sensor itself.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein:

FIGS. 7-9 illustrate the effect of shifting the magnet's position relative to the strip of the sensor of FIG. 6.

DETAILED DESCRIPTION OF THE INVENTION

As described in the Background, guided wave testing using magnetostrictive sensors is a type of nondestructive testing used for a variety of structures. Various magnetostrictive sensors and techniques are described in the following patents: U.S. Pat. No. 6,396,262 to Light, et al.; U.S. Pat. No. 6,429,650 to Kwun, et al.; U.S. Pat. No. 7,573,261 to Vinogradov; and U.S. Pat. No. 7,821,258 to Vinogradov.

The magnetostrictive sensors and methods described herein are suited for various structures, including without limitation, tubes, pipes, and plates. The sensors generate and receive guided waves, and use a ferromagnetic strip which is coupled to the surface of the structure. Thus, the structure being tested need not be ferromagnetic.

Because the structures being tested typically have two or more dimensions, for example length and width, guided wave testing is performed by sending a guided wave only in one direction. This allows the received signals to be attributed to anomalies located on one side or the other of the sensor.

Conventional Direction Control of Guided Waves

Figure 1:
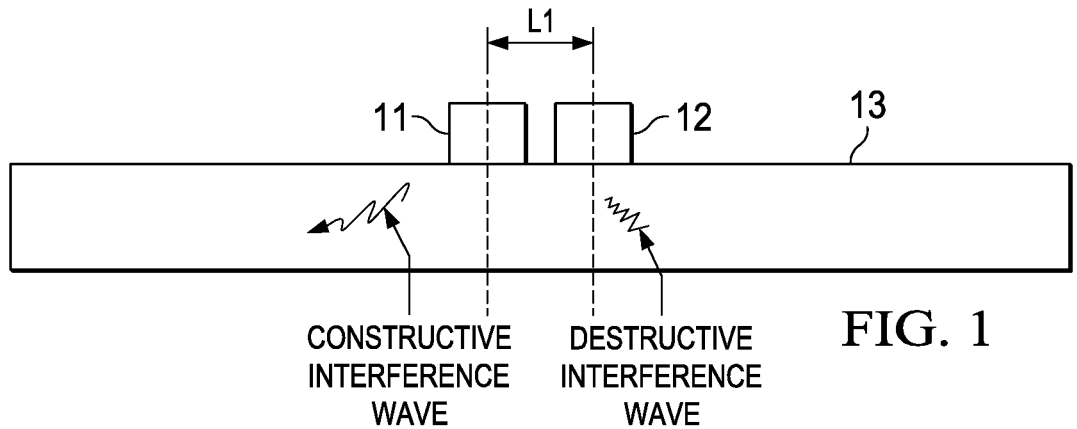
FIG. 1 illustrates a conventional method of using magnetostrictive sensors to generate a unidirectional guided wave.
Figure 2:
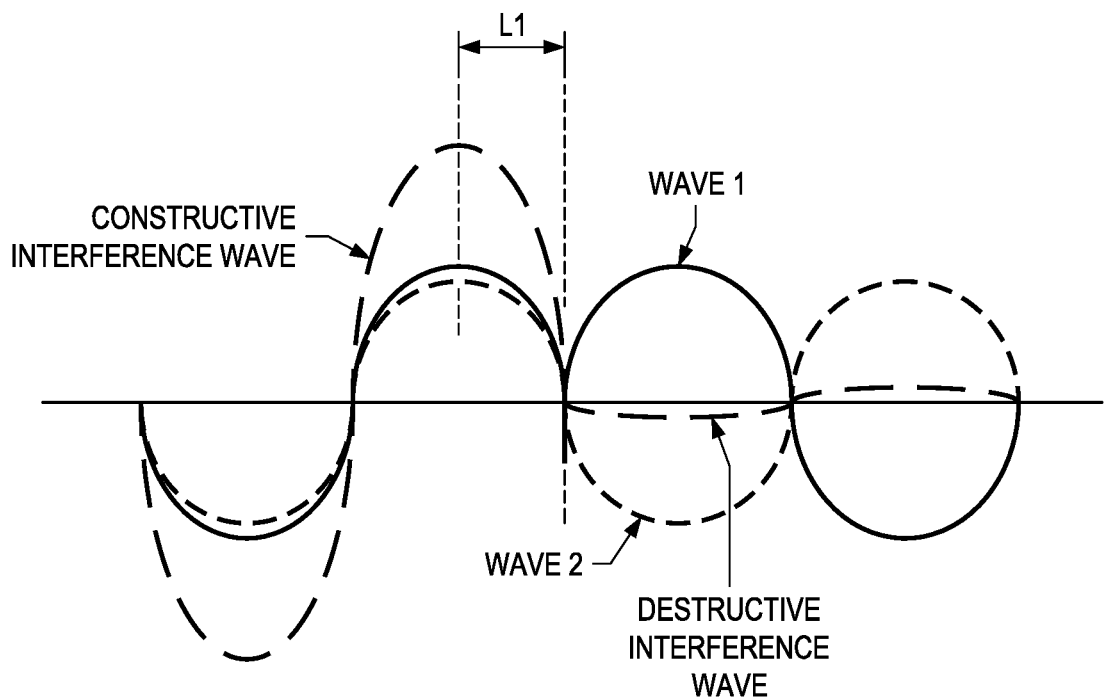
FIG. 2 illustrates the constructive and destructive interference of waves generated by the sensors of FIG. 1.

FIGS. 1 and 2 illustrate a conventional system and method for providing guided waves with a predominant direction. Two identical sensors 11 and 12 are each coupled to a structure 13. As is known, the effect of magnetostriction requires two magnetic fields (time varying and permanent magnetic bias) to be applied. For generation of transversal guided waves, the fields should be perpendicular to each other.

Various configurations may be used for each sensor 11 and 12, but in a typical configuration, a ferromagnetic strip has an AC winding, which is activated to create a time-varying magnetic field. A permanent magnet provides a magnetic bias to the ferromagnetic strip, with the magnetic field oriented in the direction of propagation of the guided wave. In operation, the sensors are activated with a 90 degrees phase delay relative to each other.

Sensors 11 and 12 are spaced a quarter wavelength of the AC excitation frequency from each other. In FIG. 1, this spacing is identified as distance L1.

As shown in FIG. 2, unidirectional propagation of the guided wave occurs as a result of destructive interference in one direction and constructive interference in the other direction. Sensor 12 is activated at a zero degree phase, and generates a guided Wave 1. Sensor 11 is activated at a 90 degrees phase, and generates guided Wave 2. Due to the quarter wavelength spacing between sensors 11 and 12, Waves 1 and 2 interfere constructively in the direction from sensor 12 toward sensor 11. In the opposite direction, Waves 1 and 2 interfere destructively.

The conventional method of FIGS. 1 and 2 allows guided waves to be sent predominantly in one or another direction. A characteristic of this conventional method is that each sensor is activated with uniform excitation throughout the sensor. In other words, for the sensor of FIG. 1, the bias magnetization provided by the permanent magnet is symmetric to both sides of the ferromagnetic strip.

Unidirectional Guided Waves with Single Sensor

Figure 3:
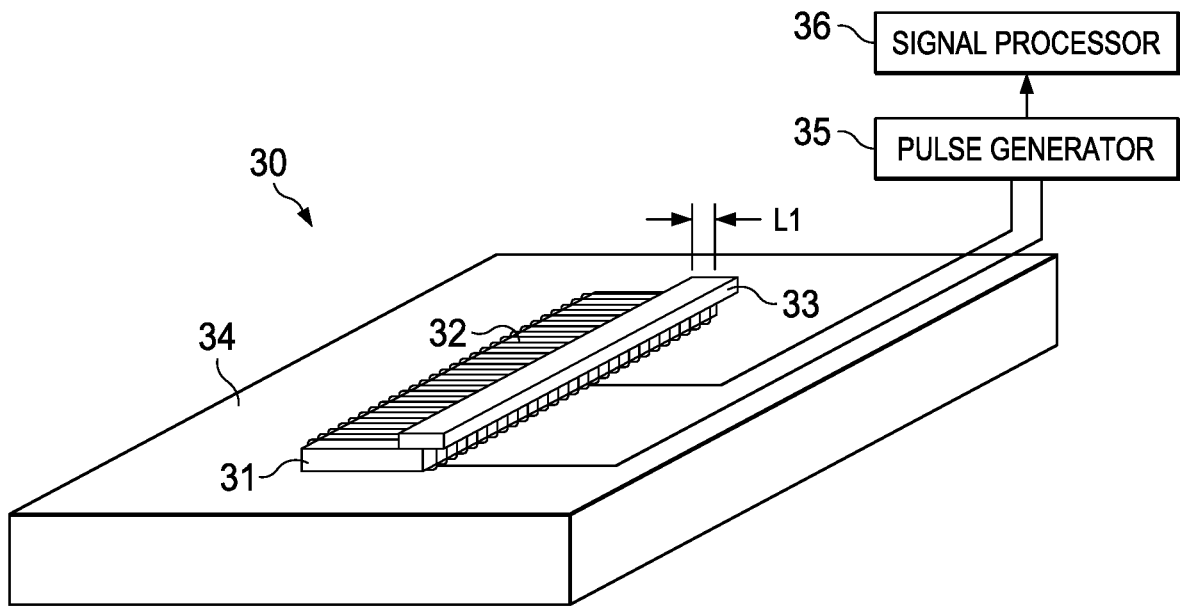
FIG. 3 is a perspective view of a magnetostrictive sensor for generating unidirectional guided waves in accordance with the invention.

FIG. 3 is a perspective view of a sensor 30 mounted on a plate structure 34, configured and operable to generate unidirectional guided waves in accordance with the invention. As explained below, sensor 30 has a ferromagnetic strip 31 that is activated with partial excitation, and the single sensor 30 generates a guided wave that is predominant in one direction.

In the example of FIG. 3, ferromagnetic strip 31 is rectangular, having a long dimension (length) and a short dimension (width). Strip 31 is typically flat on both sides (planar) and thin in the thickness dimension. Various ferromagnetic materials may be used, with a particularly suitable material being iron carbonate (FeCo).

Ferromagnetic strip 31 has an AC electric coil 32 wound around its short dimension, down the length of strip 31. When activated with an AC signal, coil 32 creates a time-varying magnetic field to make the field domain oscillate.

A permanent magnet 33 provides a magnetic bias to strip 31. In the example of FIG. 3, the magnetic field oriented in the direction of propagation of the torsional guided wave. As explained below, magnet 33 is placed atop strip 31 and coil 32, such that its pole-to-pole center is offset from the center (here longitudinal) axis of strip 31.

It should be understood that in other embodiments, strip 31 may have other geometries. In general, strip 31 has a first dimension and a second dimension. The first dimension is the dimension whose center axis is aligned with magnet 33. The coil 32 is wound around the second dimension.

Strip 31 and coil 32 are coupled to a test structure 34. A pulse generator 35 is electrically connected to coil 32 and provides an AC electrical activation signal to coil 32. Sensor 30 then produces transverse guided waves, which propagate down the length of the test structure 34. A defect in structure 34 will cause a reflection of the waves back to the sensor 30. As explained below, sensor 30 detects the reflected wave and delivers the detected signal to a signal processor 36. Signal processor 36 may be part of a comprehensive monitoring system that analyzes and reports defects in test structure 34.

Figure 4:
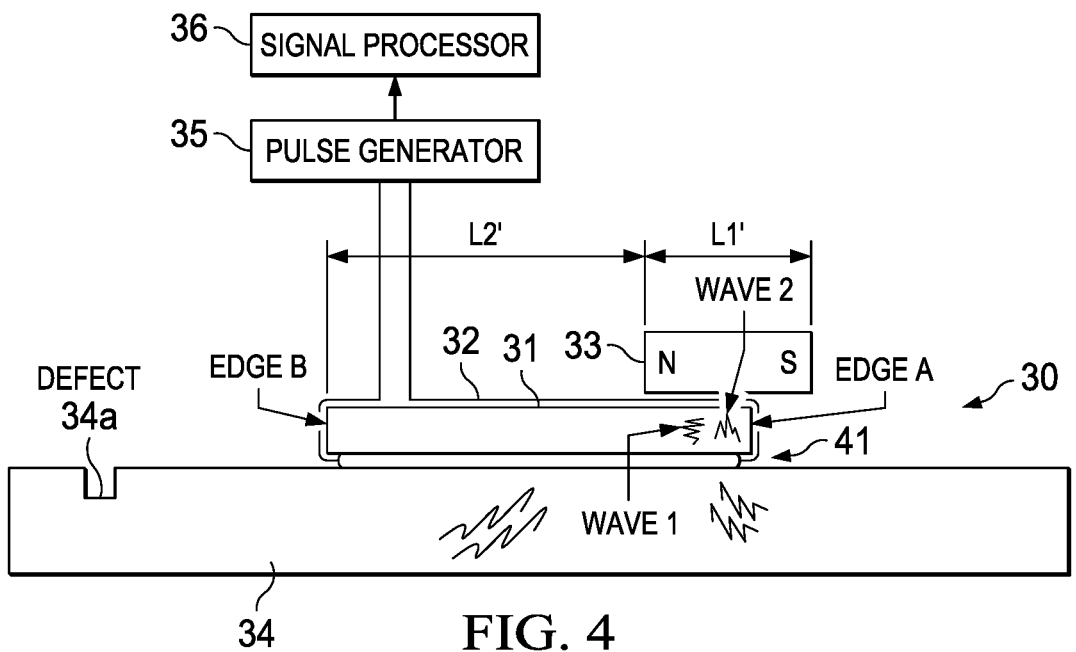
FIG. 4 is an end view, across the width, of the sensor of FIG. 3.

FIG. 4 is an end cross sectional view of sensor 30, and explains the principle of its operation. In addition to strip 31, AC winding 32, and permanent magnet 33, FIG. 4 further illustrates sensor 30 mounted on a test structure 34, with guided waves being reflected from an anomaly 34a.

A coupling interface 41 is installed between sensor 30 and the test structure 34. Coupling interface 41 is typically an epoxy or epoxy filled fiberglass. The coupling interface 41 is used to protect the AC winding 32 from mechanical damage and also to reduce impedance mismatch between the sensor and the test sample.

As indicated above in connection with FIG. 3 and as better shown in FIG. 4, magnet 33 is not as wide as strip 31. Partial excitation of strip 31 is achieved by shifting the area with permanent magnetization towards one of the edges of the strip 31. In other words, magnet 33 is offset from the center (here longitudinal) axis of strip 31, which results in more excitation of strip 31 on one side of strip 31 than the other.

In the example of FIG. 4, magnet 33 is placed along one edge of strip 31 and overhangs strip 31. In other embodiments, magnet 33 may be shifted less far from the longitudinal axis of strip 31. As explained below, the amount of offset of magnet 33 from the longitudinal axis of strip 31 may depend on the frequency of the AC excitation and the desired frequency of the guided wave to be generated. The edges of the magnet 33 and strip 31 may be aligned, the magnet 33 may overhang the strip 31, or the strip 31 may extend past the magnet 33.

In FIG. 4, the permanent magnet 33 is shifted towards Edge A of the strip 31. The width of the area of strip 31 under magnet 33 is identified as L1'. Because the permanent magnetic field is mostly presented in the area L1' of strip 31, when AC coil 32 is activated, the excitation of domain oscillations will mostly be happening under this L1' area. This is referred to as "partial excitation" of strip 31.

The partial excitation of sensor 30 may be contrasted to the uniform excitation of the sensor of FIG. 1. In FIG. 1, uniform excitation occurs because a permanent magnet is symmetric to both edges of the width of a ferromagnetic strip. The magnet is often as wide as or nearly as wide as the strip.

Figure 5:
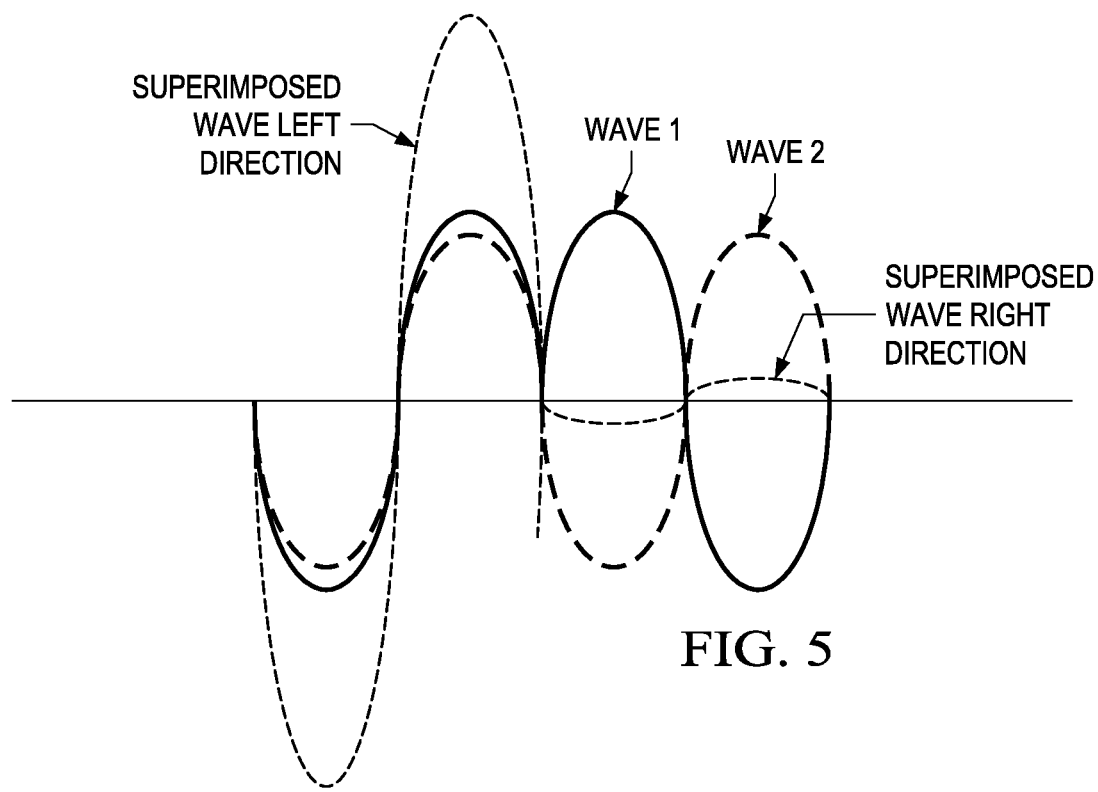
FIG. 5 illustrates the constructive and destructive interference of waves generated by the sensor of FIGS. 3 and 4.

Referring to FIGS. 4 and 5, sensor 30 generates two predominant wave fronts. One is the incident wave (Wave 1), which travels in both directions (left and right) in both the test structure 34 and in strip 31. Because Edge A is close to the point of the wave excitation, the portion of Wave 1 propagating in strip 31 will bounce off Edge A of strip 31, and will form Wave 2.

Wave 2 will superimpose Wave 1. The phase of Wave 2 will be dependent on the impedance miss-match between the edge of strip 31 and the air behind it. This parameter can vary depending on the frequency of operation. The superposition of two waves (Wave 1 and Wave 2) traveling in both directions can create the effect of constructive interference in the left direction and destructive interference in the right direction if two criteria are met: 1) the two waves are delayed by a quarter wavelength relative to each other, and 2) if there is a 90 degree phase shift between the two waves.

These two criteria are satisfied by the placement of magnet 33 relative to strip 31, and by the width of magnet 33. The quarter wavelength delay "adds" another ninety degrees to the ninety degree phase shift. The net effect is a zero degree phase shift for constructive interference and 180 degree phase shift for destructive interference.

The typical width of the area under magnet 133 should be in the order of a quarter wavelength. However, due to fact that the phase of Wave 2 can shift when frequency gets lower or higher, the actual width can be determined during sensor calibration. As explained below in connection with FIGS. 11 and 12, a single sensor configuration (with no variation of magnet width or placement) can provide a somewhat wide range of frequencies.

It should be understood that the constructive and destructive interference need not be "maximum" (zero and 180 degrees out of phase) so long as the ratios of the constructively and destructively interfered waves allow them to be distinguished from each other. The constructive interference wave is predominant, and is referred to herein as a "unidirectional" guided wave.

In practice, unidirectional propagation of guided waves based on partial excitation of strip 31 can be confirmed in a rather wide frequency range. The width of magnet 33 (and hence the area of excitation under magnet 33) and the offset of magnet 33 relative to the longitudinal axis of strip 31 can be adjusted for a desired frequency. The practical range for unidirectional guided wave generation was found by experimentation to be 60-700 kHz.

FIGS. 6-9 illustrate the effect of shifting the magnet relative to the ferromagnetic strip of sensor 30. Although not explicitly shown, sensor 30 has the elements illustrated in FIGS. 3 and 4. AC coil 32 was activated at a 500 kHz frequency.

Figure 6:
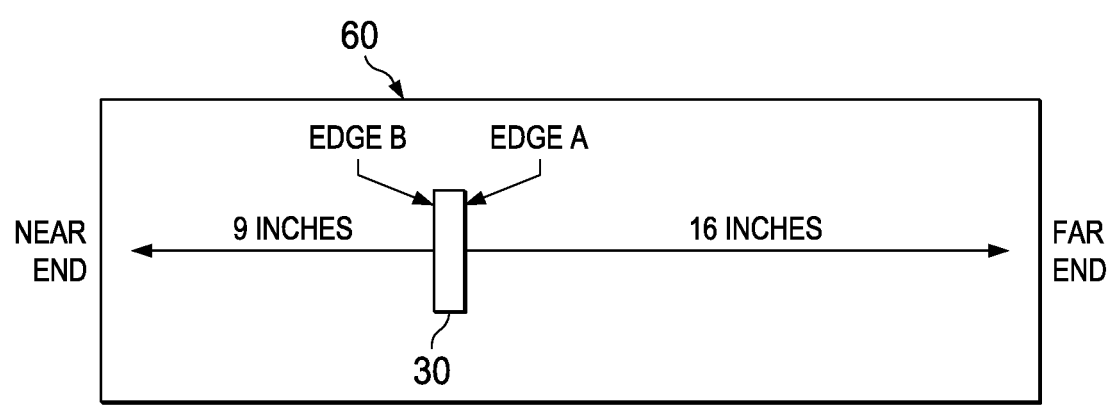
FIG. 6 illustrates an example of the sensor of FIGS. 3 and 4, placed on a test structure.

FIG. 6 is a top view of sensor 30 placed on a test structure 60. In this example, test structure 60 is an aluminum plate having a thickness of 3 mm. Sensor 30 is placed on plate 60 at a distance of 9 and 16 inches, respectively, from two opposing edges of structure 60. These edges of plate 60 are identified as the "near end" and "far end", indicating whether they are more near or more far from sensor 30.

FIG. 7 illustrates guided wave reflections from the near and far end of plate 60 when magnet 33 symmetrically biases both sides of strip 31. The entire strip 31 is activated. Both end reflections have similar amplitudes.

FIG. 8 illustrates guided wave reflections from the near and far end of plate 60 when magnet 33 was shifted towards Edge B of strip 31. Thus only Edge B is activated, and only a far end reflection is observed.

FIG. 9 illustrates guided wave reflections from the near and far end of plate 60 when magnet 33 was shifted towards Edge A of strip 31. Only Edge A is activated, and only a near end reflection is observed.

Figure 10:
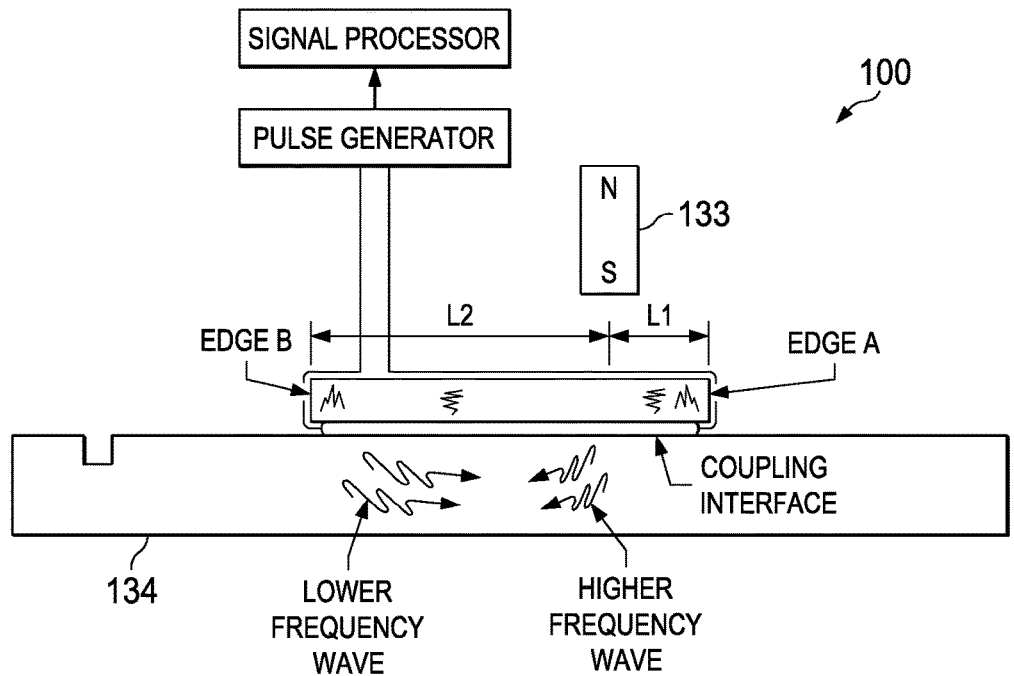
FIG. 10 illustrates a sensor configured to provide two guided waves traveling in opposite directions, but in different frequency ranges.

FIG. 10 illustrates a sensor 100 configured to provide two guided waves traveling in opposite directions, but in different frequency ranges. Sensor 100 has its magnet 133 oriented vertically, with one pole against strip 131 and the other pole distal to strip 131. In other words, the opposing poles are perpendicular to the direction of the short dimension of the strip 131.

The distance from magnet 133 to a first edge of strip 131, Edge A, is L1. The distance from magnet 133 to the opposing edge of strip 131, Edge B, is L2. Both areas L2 and L1 will be magnetized about the same. Because area L2 is longer, constructive interference with the wave bouncing off Edge 2 will occur at a lower frequency. At the same time, constructive interference with the wave bouncing off Edge 1 will occur at a higher frequency. The two higher and lower frequency waves will travel in opposite directions.

Figure 11:
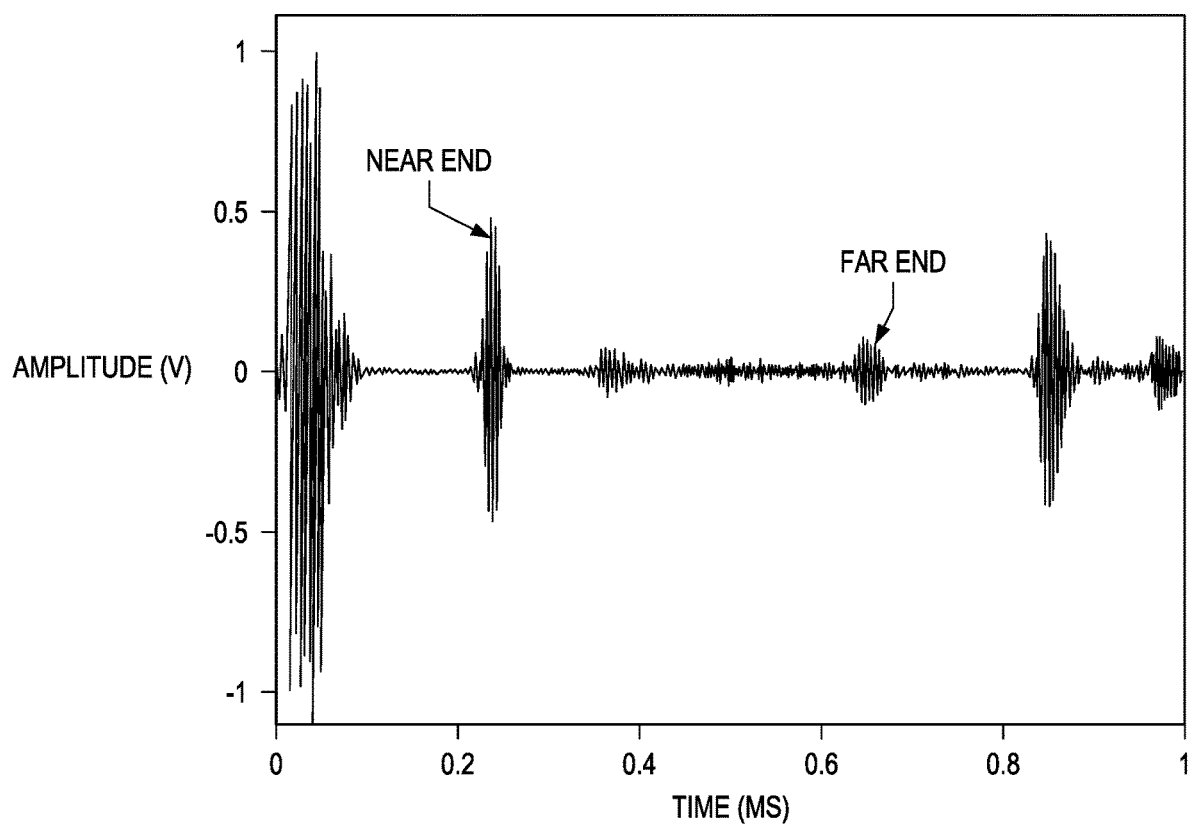
FIGS. 11 and 12 illustrate signals obtained from the same sensor, but with different excitation frequencies at different times.
Figure 12:
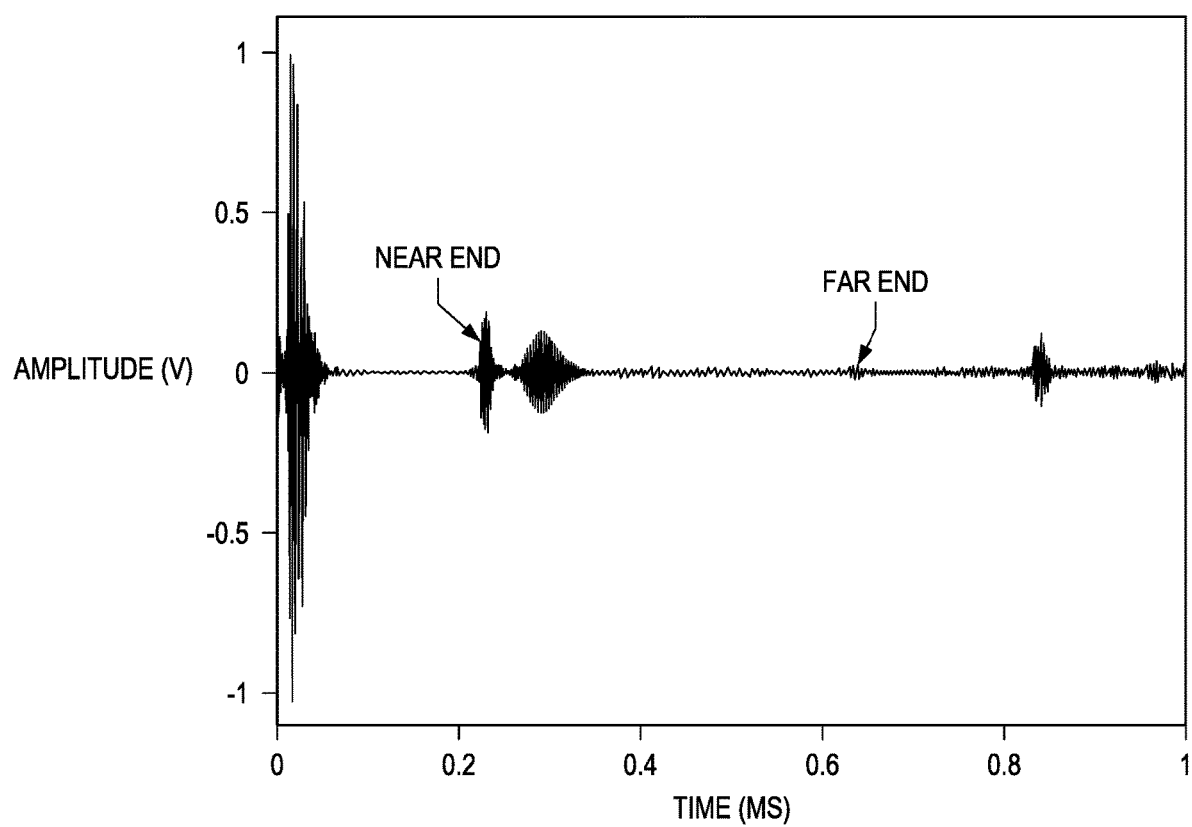

FIGS. 11 and 12 illustrate signals obtained from the same sensor, but with different excitation frequencies at different times. The sensor was configured with a permanent magnet covering a width of 0.25 inches at one side of strip 31. Sensor 30 was configured to send the directional guided waves towards the near end of the plate. The center frequencies are 200 kHz (FIG. 11) and 430 kHz (FIG. 12).

For both frequencies, the ratio between the near end and far end of the signal is good, which indicates that direction control in the entire frequency range is obtainable. Thus, the width of the strip under magnet and the extent of the magnet's offset need not result on maximum constructive and destructive interference. It is sufficient that the constructive and destructive interference produce signal ratios that allow the waves from the two directions to be distinguished from each other. Further, based on signals presented at the higher frequency (430 kHz), this directional operation of probe 30 is applicable to both of the two lower shear horizontal modes (SH0 and SH1).

Figure 13:
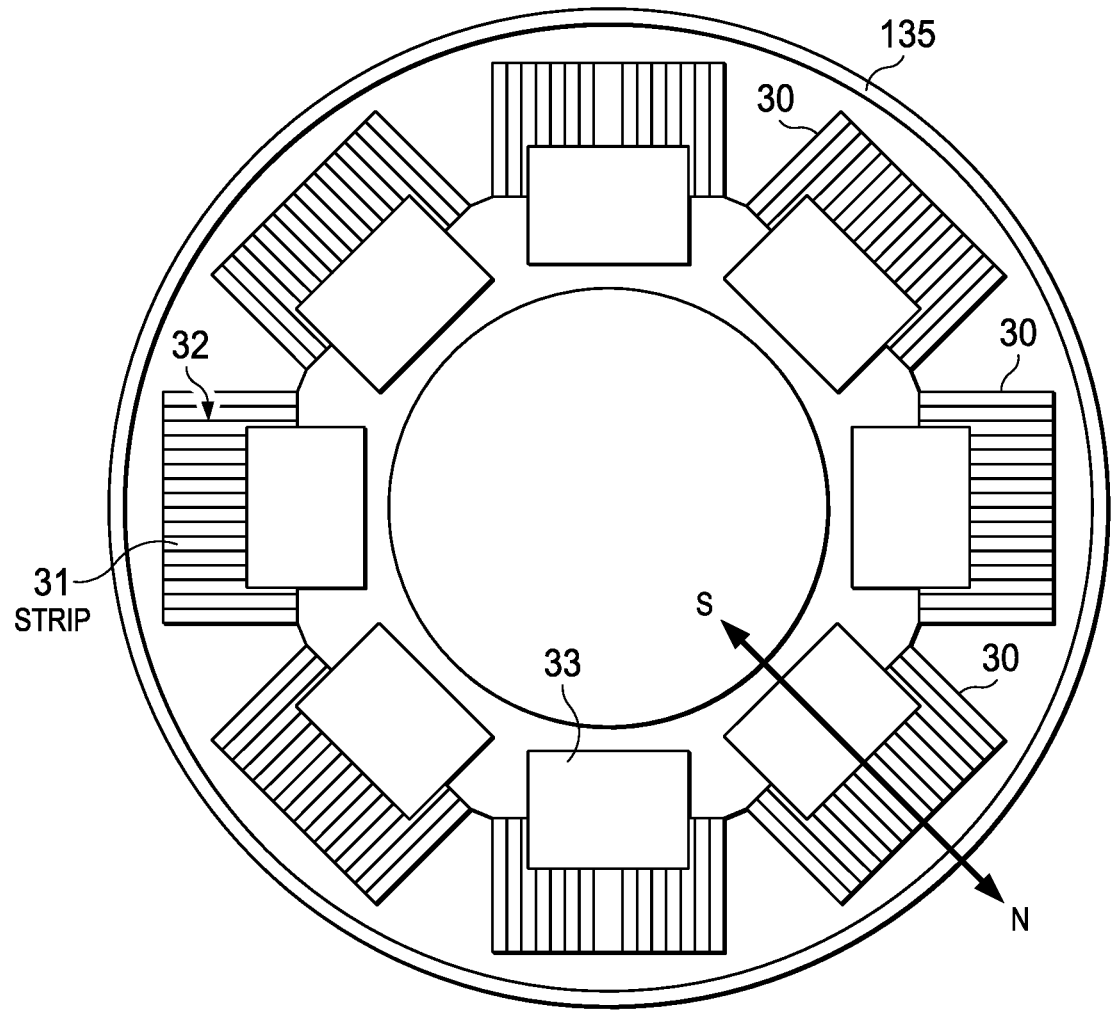
FIG. 13 illustrates how a number of sensors can be arranged to provide omnidirectional coverage for a plate structure.

FIG. 13 illustrates how a number of sensors 30 can be arranged to provide omnidirectional coverage for a plate structure. A frame 135 supports a circular array of eight sensors 30, which are shown in plan view. Each sensor 30 has the elements of sensor 30 of FIGS. 3 and 4. For sending guided waves outwards from the array, the magnet 33 of each sensor 30 is offset toward the edge of the strip 31 that faces the center of the array.

In operation, the array is coupled to a plate structure (not shown). When activated, each sensor 30 tests a 45 degree segment of the plate structure. Switching the pulse generator from sensor to sensor in a sequence allows omnidirectional coverage of the plate. Because only one segment is tested at a time, a significant reduction of spurious signals coming from other directions can be accomplished.

Figure 14:
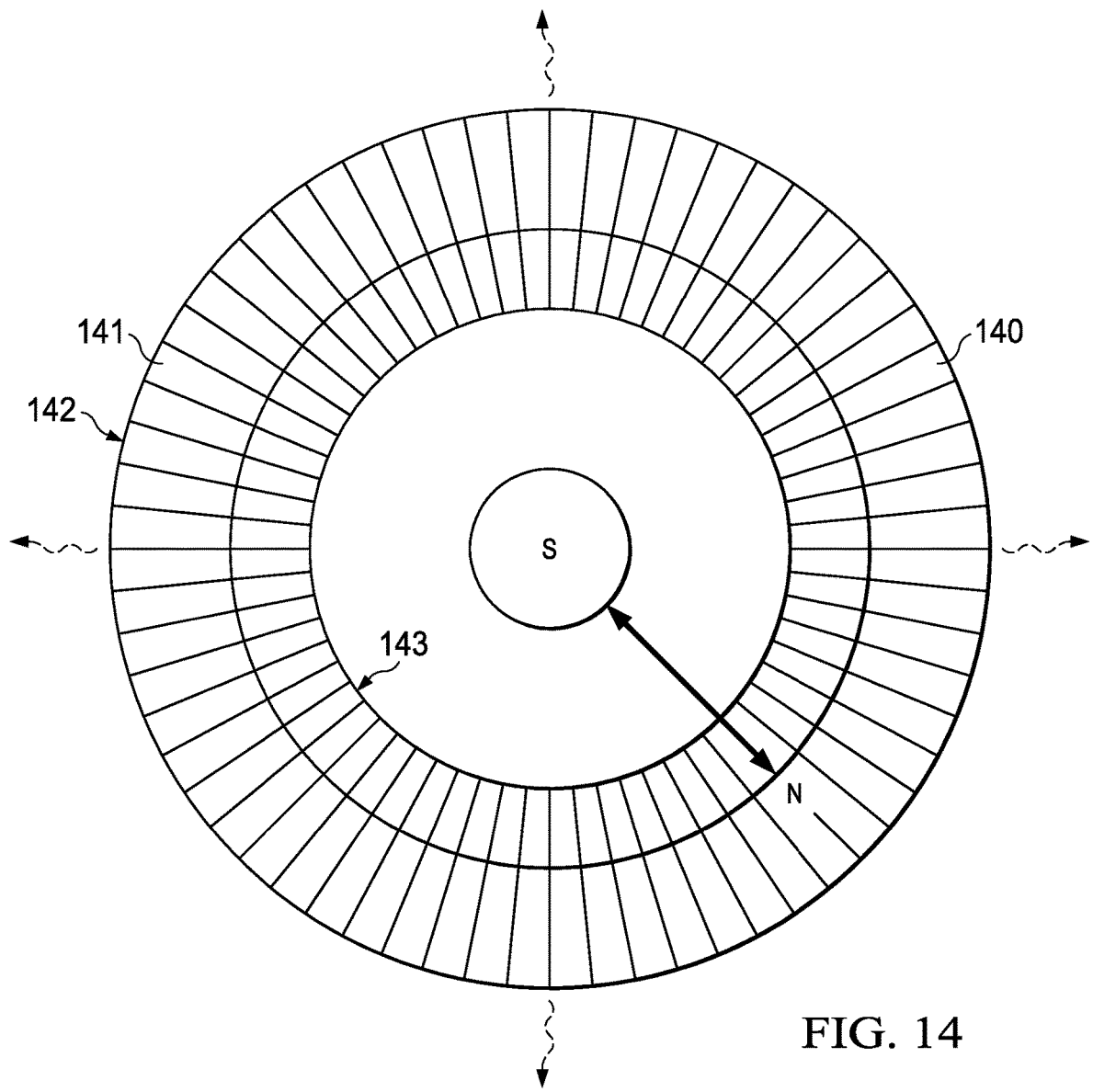
FIG. 14 illustrates a modification of the array of FIG. 13.

FIG. 14 illustrates a variation of the sensor array of FIG. 13, also used for plate structures. Eight sensors 140 are arc shaped, each with its magnet 143 offset toward the center of the array. In implementation, the magnets 143 can form a single integrated magnet ring. The strip 141 of each sensor is also arc shaped, with a coil winding 142. The arc shaped sensors 143 provide a uniform energy distribution around the array.

Figure 15:
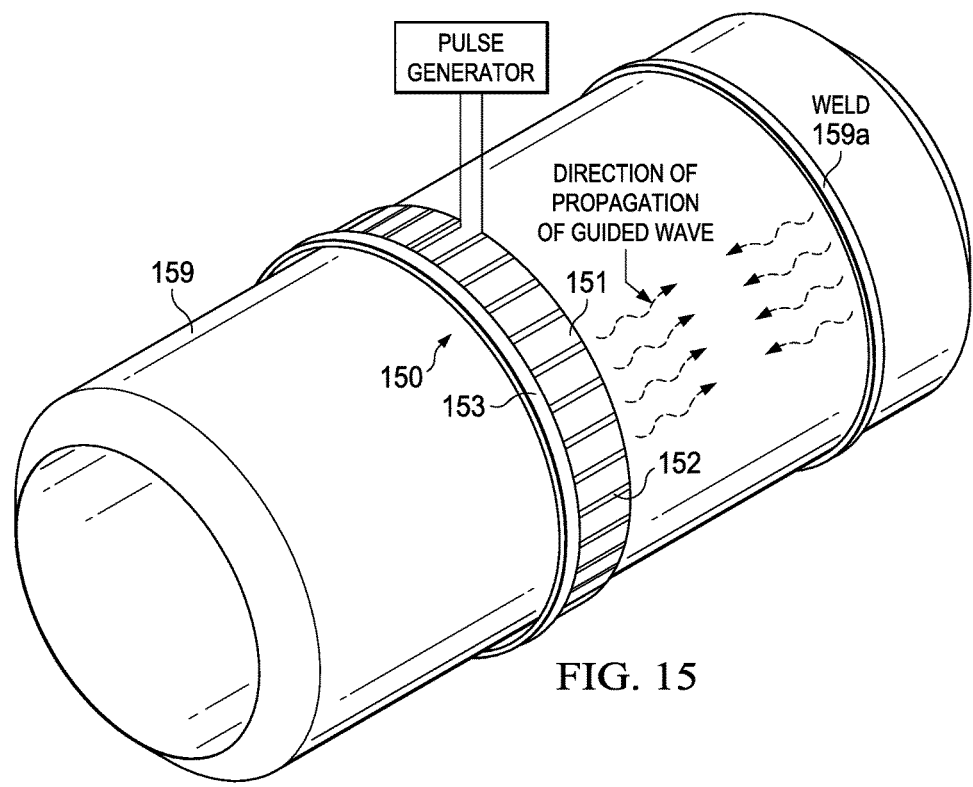
FIG. 15 illustrates an embodiment of the invention designed for testing pipes.

FIG. 15 illustrates an embodiment of the invention specifically designed for use in guided wave testing of pipes and similar elongated structures. Sensor 150 is flexible and configured to wrap around the circumference of a pipe 159. The length of ferromagnetic strip 151 wraps in a belt-like manner around the circumference with a small gap at the ends. An AC coil 152 is wound around the width of strip 151. A permanent magnet 153 is against strip 151, also around the entire circumference, and is offset to one side of strip 151.

Because sensor 150 can provide a very broadband signal generation, it can be installed permanently next to an area of interest, such as a weld 159a, to monitor its condition. Also, AC winding 152 could be segmented to multiple windings, each activated separately and responsible only for a certain area of the weld.

Figure 16:
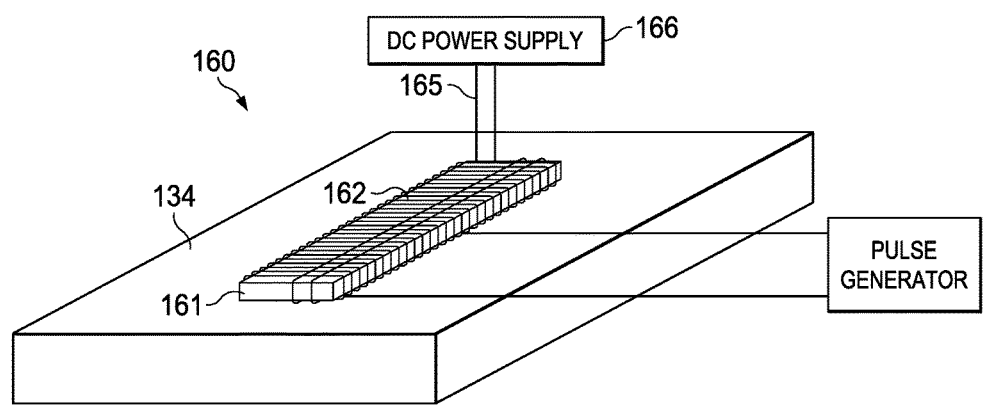
FIG. 16 illustrates a sensor similar to the sensor of FIG. 3, but with the permanent magnet replaced by an electromagnet.

FIG. 16 illustrates a sensor 160, which is similar to sensor 30, but with the permanent magnet replaced by an electromagnet 163. As with sensor 30, a ferromagnetic strip 161 is wound with an AC coil 162. A DC bias coil 165 is wound around strip 161, with the windings being parallel to strip 161. DC bias coil 165 is connected to a DC power supply 166, which provides the excitation for electromagnet 163.

DC bias coil 165 introduces a magnetic field that is offset from the center axis of strip 161, analogous to the one produced by the permanent magnet described above. DC bias coil 165 may be placed near the edge of the strip 161, and can be placed on top of the strip 161 or on both sides of the strip 161.

In variations of sensor 160, multiple DC bias coils can be used, and their selective activation can determine both the width of strip 161 that is partially activated, as well as the offset of the activation.

What is claimed is:

1. A sensor for use in magnetostrictive testing of a structure, comprising:
   a strip made from a ferromagnetic material, and having a first dimension and a second dimension, the first dimension having a center axis;
   an electrical coil wrapped around the second dimension of the strip;
   a magnet attached to the strip located along the first dimension of the strip but offset from the center axis, such that the magnet asymmetrically magnetizes the second dimension of the strip;
   wherein the magnet is arranged in a fixed location relative to the strip to produce, upon excitation of the electrical coil, a first wave that travels in opposite directions within the strip, and in one of the directions is reflected by an edge of the strip to form a second wave that constructively superimposes the first wave in the other of the directions;

wherein the sensor is operable to generate guided waves that travel within the structure and remain predominant in one direction within the structure.

2. The sensor of claim 1, wherein the magnet is a permanent magnet.

3. The sensor of claim 2, wherein the magnet is polarized with opposing poles in the direction of the second dimension of the strip.

4. The sensor of claim 2, wherein the magnet is polarized with opposing poles perpendicular to the direction of the second dimension of the strip.

5. The sensor of claim 1, wherein the magnet is an electromagnet.

6. The sensor of claim 1, wherein the strip and the magnet are planar.

7. The sensor of claim 1, wherein the strip and the magnet are ring shaped.

8. The sensor of claim 1, wherein the magnet has a width equal to one quarterwave length of an expected activation signal.

9. The sensor of claim 1, wherein the first wave and the second wave are delayed by a quarter wavelength relative to each other, and there is a 90 degree phase shift between the first wave and the second wave.

10. A method of using a magnetostrictive sensor for testing of a structure, comprising:

placing a magnetostrictive sensor against the surface of the structure, the sensor comprising a strip made from a ferromagnetic material, and having a first dimension and a second dimension, the first dimension having a center axis; an electrical coil wrapped around the second dimension of the strip; a magnet attached to the strip located along the first dimension of the strip but offset from the center axis, such that the magnet asymmetrically magnetizes the second dimension of the strip; wherein the magnet is arranged in a fixed location relative to the strip to produce, upon excitation of the electrical coil, a first wave that travels in opposite directions within the strip, and in one of the directions is reflected by an edge of the strip to form a second wave that superimposes the first wave in the other of the directions;

applying an AC current to the coil;

wherein the sensor is operable to generate guided waves that travel within the structure and remain predominant in one direction within the structure.

11. The method of claim 10, wherein the magnet is a permanent magnet.

12. The method of claim 11, wherein the magnet is polarized with opposing poles in the direction of the second dimension of the strip.

13. The method of claim 11, wherein the magnet is polarized with opposing poles perpendicular to the direction of the second dimension of the strip.

14. The method of claim 1, wherein the magnet is an electromagnet.

15. The method of claim 14, wherein the magnet is an electromagnet provided by winding the strip with a DC bias coil, and further comprising the step of providing additional DC bias coils such that the width and locations of the electromagnet may be varied.

16. The method of claim 10, wherein the structure is cylindrical and the sensor is ring shaped.

17. The method of claim 10, wherein the structure is planar and the sensor is planar.

18. The method of claim 10, wherein the placing step is repeated by placing a number of sensors in a ring, and wherein the step of applying an AC current is repeated for each sensor.

19. The method of claim 10, wherein the magnet has a width equal to one quarterwave length of an expected activation signal.

20. The method of claim 10, wherein the first wave and the second wave are delayed by a quarter wavelength relative to each other, and there is a 90 degree phase shift between the first wave and the second wave.

* * * * *